(12) United States Patent
Miyasaka

(10) Patent No.: US 8,603,072 B2
(45) Date of Patent: Dec. 10, 2013

(54) MALE CONNECTOR AND TRANSFUSION LINE CONNECTION APPARATUS EQUIPPED WITH MALE CONNECTOR

(75) Inventor: Susumu Miyasaka, Tokyo (JP)

(73) Assignee: Covidien LP, Mansfield, MA (US)

( * ) Notice: Subject to any disclaimer, the term of this patent is extended or adjusted under 35 U.S.C. 154(b) by 117 days.

(21) Appl. No.: 13/156,510

(22) Filed: Jun. 9, 2011

(65) Prior Publication Data
US 2011/0306940 A1 Dec. 15, 2011

(30) Foreign Application Priority Data
Jun. 14, 2010 (JP) .................... 2010-134713

(51) Int. Cl.
A61M 25/18 (2006.01)
(52) U.S. Cl.
USPC ........... 604/537; 604/249; 604/533; 604/534; 251/149.1; 251/149.5
(58) Field of Classification Search
USPC .................... 604/167.04, 249, 533, 534, 537; 251/149.1
See application file for complete search history.

(56) References Cited

U.S. PATENT DOCUMENTS

| | | | |
|---|---|---|---|
| 4,398,544 A | 8/1983 | Nugent et al. | |
| 5,122,123 A | 6/1992 | Vaillancourt | |
| 5,125,415 A | 6/1992 | Bell | |
| 5,405,323 A * | 4/1995 | Rogers et al. | 604/508 |
| 5,738,144 A | 4/1998 | Rogers | |
| 6,869,426 B2 | 3/2005 | Ganem | |
| 7,004,934 B2 | 2/2006 | Vaillancourt | |
| 7,396,051 B2 | 7/2008 | Baldwin et al. | |
| 7,500,961 B2 | 3/2009 | Nemoto | |
| 7,588,563 B2 | 9/2009 | Guala | |
| 7,666,170 B2 | 2/2010 | Guala | |
| 7,753,892 B2 | 7/2010 | Newton et al. | |
| 2002/0128604 A1* | 9/2002 | Nakajima | 604/164.01 |
| 2003/0032940 A1 | 2/2003 | Doyle | |
| 2003/0060804 A1 | 3/2003 | Vaillancourt | |
| 2003/0093061 A1 | 5/2003 | Ganem | |
| 2004/0124389 A1 | 7/2004 | Phillips | |
| 2004/0172006 A1 | 9/2004 | Bonaldo | |
| 2005/0087715 A1 | 4/2005 | Doyle | |
| 2005/0090805 A1 | 4/2005 | Shaw et al. | |
| 2005/0228362 A1 | 10/2005 | Vaillancourt | |
| 2007/0043334 A1 | 2/2007 | Guala | |
| 2007/0161970 A1 | 7/2007 | Spohn et al. | |

(Continued)

FOREIGN PATENT DOCUMENTS

EP 0798013 10/1997
WO WO 2006074935 1/2006

Primary Examiner — Emily Schmidt
(74) Attorney, Agent, or Firm — Lisa E. Winsor, Esq.

(57) ABSTRACT

The male connector of the present disclosure allows for the flow of fluids therethrough and includes a movable blunt needle having a shoulder projecting radially outwards from the movable blunt needle. The male connector also includes an outer cylinder body formed around the movable blunt needle and disposed in coaxial alignment to the movable blunt needle, a blunt needle retainer which retains the movable blunt needle so that the movable blunt needle can move in an axial direction, and a valve which opens as a result of the movable blunt needle moving in the axial direction when the posterior end presses against the valve. This occurs when the movable blunt needle is inserted into a corresponding connection site, such as a female connector, and the shoulder presses against the connection site to force the movable blunt needle in the axial direction.

20 Claims, 6 Drawing Sheets

(56) References Cited

U.S. PATENT DOCUMENTS

| | | |
|---|---|---|
| 2008/0200902 A1 | 8/2008 | Mabuchi |
| 2008/0208132 A1* | 8/2008 | Funamura et al. ....... 604/167.03 |
| 2008/0249508 A1 | 10/2008 | Lopez et al. |
| 2009/0292274 A1 | 11/2009 | Guala |

* cited by examiner

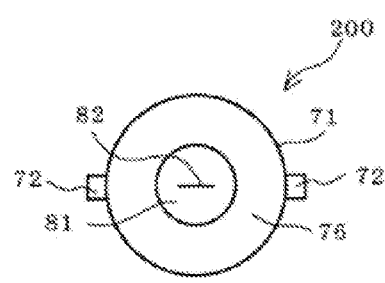 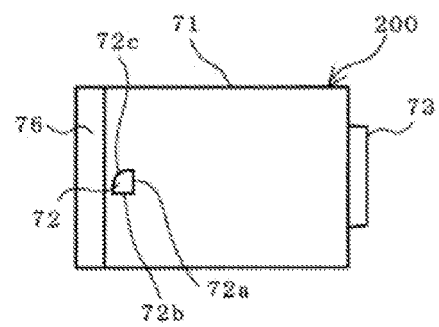
FIG. 4A　　　　　　　FIG. 4B
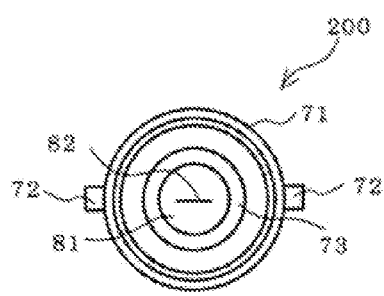 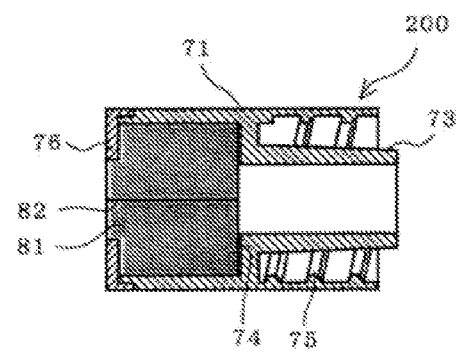
FIG. 4C　　　　　　　FIG. 4D

MALE CONNECTOR AND TRANSFUSION LINE CONNECTION APPARATUS EQUIPPED WITH MALE CONNECTOR

BACKGROUND

1. Technical Field

The present disclosure relates to a male connector of a transfusion line which conducts fluids such as drug solutions to patients and transfusion line connection apparatus for use with the connector cap.

2. Background of the Related Art

During conventional medical procedures, medical fluids such as drug solutions and blood, etc. are supplied to a patient by a transfusion system through a tube. Within this type of transfusion system, connection equipment is used to provide throughflow between tubes by including male and female connectors at the end of the tubes.

A transfusion system that can prevent leaks is desirable to prevent fluid from contacting medical staff and patients. This is important because medical fluids that are supplied by the transfusion system, such as anti-cancer and transfusion drugs, may have induced characteristics or may cause side effects such as cytopathy, genotoxicity, carcogenicity, and fetal malformation.

A male connector with the purpose of preventing medical fluid from leaking when being disconnected from a female connector is proposed in Japanese Unexamined Patent Application Publication No. 2006-102254 ("JP 2006-102254"). The male connector of JP 2006-102254 is equipped with a cylindrical injector which has an opening on the peripheral wall at the end and a protective shutter that moves along the injector to open and close the aperture. The protective shutter is positioned to block the aperture and is openend when it receives an indentation force towards a base portion. The protective shutter once again blocks the aperture when the indentation force is released.

In JP 2006-102254 the protective shutter is made from an elastic body covers the opening. However, this protective shutter only retains the injector by the radial constriction flexibility of the injector. Therefore, it is likely that the protective shutter would shift towards the axis and open the aperture. Also, since the protective shutter moves along the axis of the injector with an enlarged diameter when the male and female connectors are attached or detached, it is easy to deform and collapse. If the flexibility of the protective shutter collapses, the aperture cannot be appropriately covered. Leaks may occur from the aperture.

Another male connector with a male lure which can be connected to a female lure and having a "tubular elastic body 15" positioned between the inlet and outlet is proposed in European Published Application No. EP 1,747,796 A1. This "tubular elastic body 15" is equipped with a "diaphragm 22" which normally blocks the inlet and outlet of the male connector. However, when the male lure is connected to the female lure, the "incision 23" of the "diaphragm 22" opens so that a flow path forms between the inlet and outlet, as described in European Published Application No. EP 1,747,796 A1.

SUMMARY

The present disclosure provides a male connector that can control leaks when not connected to the female connector, can reduce the endurance fatigue of a seal member used to controls the leaks, and provides a transfusion line connection apparatus for use with the male connector.

The male connector provides a flow path for medical fluids and includes a movable blunt needle having a shoulder projecting radially outwards from the movable blunt needle. The shoulder is installed at the predetermined axial position to limit movement in the axial direction. The male connector also includes an outer cylinder body formed around the movable blunt needle and disposed in coaxial alignment with the movable blunt needle, a movable blunt needle retainer which retains the movable blunt needle, and a valve which opens as a result of the movable blunt needle moving in the axial direction such that the posterior end of the movable blunt needle presses against the valve to open the valve. This occurs when the movable blunt needle is inserted into a corresponding connection site, such as a female connector, and the shoulder presses against the connection site to force the movable blunt needle in an axial direction relative to the outer cylinder body such that the posterior end presses against the valve.

The male connector may include a movement regulation section at the exterior portion of the movable blunt needle which regulates or limits the movement of the movable blunt needle in the axial direction when the posterior end is positioned such that the valve is opened.

The peripheral tip of the outer cylinder body of the male connector has a locking section demarcated by a locking groove that engages a protrusion of corresponding connector by circumferential rotation at the locking section. The locking surface and the hooked surface extending from the locking surface are formed corresponding to a circumferential direction, and a connection with the corresponding connector is fixed by the engaging the locking section with the protrusion of the corresponding connector.

The transfusion line includes the male connector, as described above, and a female connector. The female connector includes a septum having an insertable connection tube positioned on the outer cylinder body section of the female connector and seal inside of the connection tube where a slit is formed for the reception of the movable blunt needle of the male connector. When the movable blunt needle is inserted into the slit of the female connector the movable blunt needle moves in the axial direction at the posterior end to open the valve of the male connector due to the shoulder contacting the septum. In this way the inlet channel of the movable blunt needle is open and medical fluids can flow through the male and female connectors.

The movable blunt needle of the male connector is positioned so that the movable blunt needle has a flow path which can be moved in the axial direction relative to the movable blunt needle retainer. The male connector includes a valve which is positioned at the posterior end such that the flow channel inlet of the movable blunt needle is blocked. The valve is opened as a result of the posterior end of the movable blunt needle pressing against the valve when the movable blunt needle is moved in the axial direction. When the movable blunt needle is inserted into the corresponding connector, it moves in the axial direction and opens the valve due to the shoulder being in contact with the corresponding connector. This causes the flow channel inlet of the movable blunt needle to be open thereby allowing medical fluids to flow between the male connector and the corresponding connector. Thus, when removing the male connector from the corresponding connector, fluid leaks are inhibited from the male connector. In addition, the valve is deformed only when the movable blunt needle is moved in the axial direction and the posterior end presses against the valve, in other words, only when the male connector is connected to the corresponding connector. Because of this amount of deformation that the valve undergoes is minimal and thus endurance fatigue of the valve can be minimized.

The male connector may alternately have a movement regulation section provided at the periphery of the movable blunt needle. The movement regulation section limits movement towards the valve in the axial direction. This prevents excessive movement of the movable blunt needle towards the valve.

The peripheral tip of the outer cylinder body of the male connector has a locking section demarcated by a locking groove that engages the protrusion of a corresponding connector by circumferential rotation. The locking surface and the hooked surface extending from the locking surface are formed corresponding to a circumferential direction, and a connection with the corresponding connector is fixed by the engaging the locking section with the protrusion of the corresponding connector. Therefore, the distance between the connected male connector and the corresponding connector can be controlled, and the flow of fluids between the male connector and the corresponding connector can be maintained in a stable manner.

BRIEF DESCRIPTION OF THE DRAWINGS

Various embodiments of the present disclosure are described herein below with references to the drawings, wherein:

FIGS. 4A-4D are diagrams showing the front, side, rear, and sectional surface of the female connector according to embodiment 1;

DETAILED DESCRIPTION OF THE EMBODIMENTS

Figure 1:
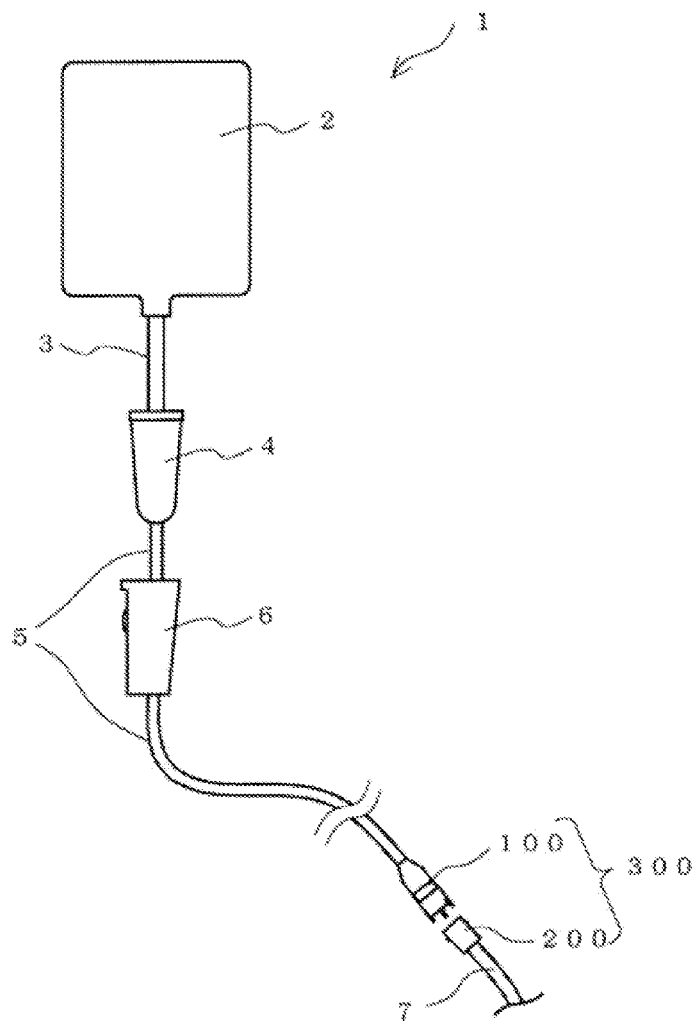
FIG. 1 is a schematic diagram showing the transfusion line set structure according to embodiment 1.

In the drawings and in the description which follows, in which like references numerals identify similar or identical elements, the term "proximal" will refer to the end of the apparatus which is closest to the clinician during use, while the term "distal" will refer to the end which is furthest from the clinician, as is traditional and known in the art.

Embodiment 1

FIG. 1 shows an example of the structure of the transfusion line set according to embodiment 1. The transfusion line set 1 is adapted to supply medical fluid such as a drug solution, etc., and includes a fluid container 2 which contains the medical fluid, a tube 3, an infusion tube 4, a tube 5, a roller clamp 6, a transfusion line connection apparatus 300 including a male connector 100 and a female connector 200, and a tube 7.

Fluid container 2 is a container for storing various medical fluids such as drug solutions, nutrients, anti-cancer drugs, saline, and blood. Infusion tube 4 temporarily accumulates the drug solution supplied from liquid container 2 through tube 3 as well as sending a predetermined amount of the medical fluid to roller clamp 6 through tube 5. Roller clamp 6 is adapted for regulating the flow of the medical fluid supplied through tube 5 by compressing soft tube 5. If tube 5 is compressed to the maximum, the flow of medical fluid can be halted.

Male connector 100 is attached to the downstream end of tube 5 and female connector 200 is attached to tube 7. By connecting male connector 100 with female connector 200, tube 5 and tube 7 connect.

Figure 2A:
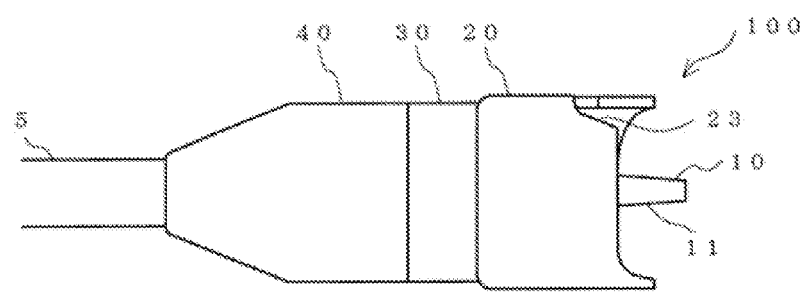
FIGS. 2A and 2B are diagrams showing the front surface and side surface of the male connector according to embodiment 1.
Figure 2B:
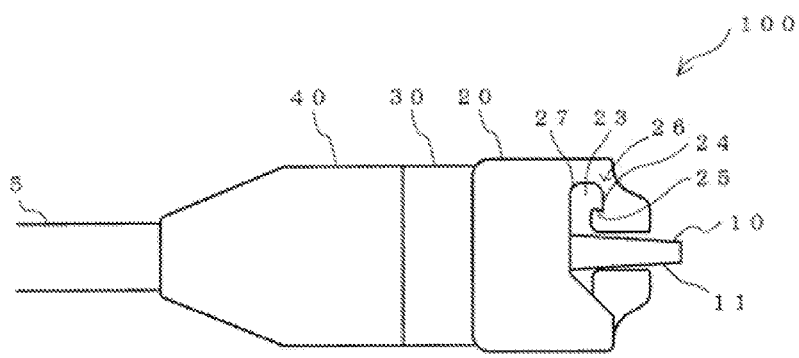
Figure 3A:
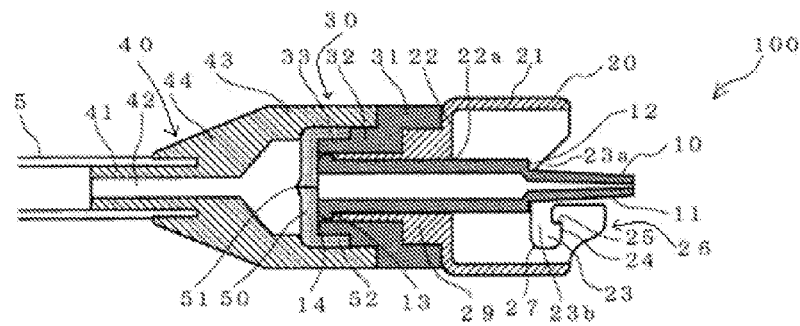
FIGS. 3A-3C are cross-sections of the male connector according to embodiment 1.
Figure 3B:
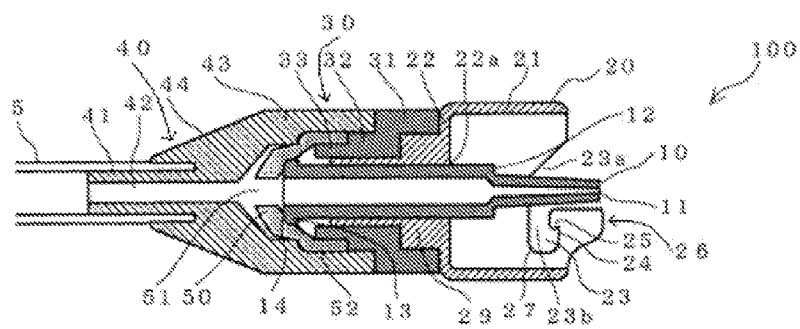
Figure 3C:
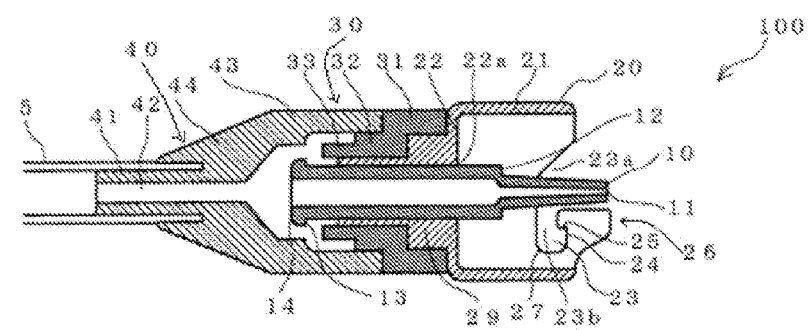

FIGS. 2A-2B show male connector 100; FIG. 2A shows a front surface and FIG. 2B shows a side surface. FIGS. 3A-3C are cross-sectional drawings of male connector 100; FIG. 3A shows the movable blunt needle 10 being set in the axial direction at the front end, FIG. 3B shows the movable blunt needle 10 being positioned in the axial direction at the posterior end, and FIG. 3C shows FIG. 3B without valve 50 for the sake of explanation. In FIGS. 2A-2B and 3A-3C, the right side of the figures is the front end and the left side of the figures is the posterior end.

Male connector 100 includes a movable blunt needle 10, which allows the flow of fluids, an outer cylinder body 20, which is formed outside movable blunt needle 10 and is almost coaxial with movable blunt needle 10, a cylindrical junction 40 which is adapted for connection to tubes and catheters, etc., and a link section 30 which links cylinder body 20 and junction 40. In addition, there is a valve 50 disposed between cylinder body 20 and junction 40 so that the posterior end (flow channel inlet) of the movable blunt needle is blocked.

The front end of movable blunt needle 10 has a blunt needle section 11 for insertion into the female connector 200. At around the middle of the axis of the movable blunt needle, a shoulder 12 is formed and projects radially outward. The outside diameter of shoulder 12 is larger than that of blunt needle section 11. At the posterior end of the movable blunt needle 10, a flange 13 is formed which expands radially outward. The posterior end of flange 13 is a compressed valve surface 14 defining a chamfered cross section having an arcuate shape.

Cylinder body 20, which is formed outside movable blunt needle 10 and almost coaxial with the movable blunt needle 10, includes an outer cylinder 21 surrounding movable blunt needle 10 and a bottom 22 extending inward from outer cylinder 21 and having a roughly cylindrical shape. Hole 22a is formed almost at the center of bottom 22 and is adapted to receive movable blunt needle 10. The diameter of hole 22a, is large enough to form a liquid tight seal between movable blunt needle 10 and hole 22a while allowing axial movement of movable blunt needle 10. Blunt needle retainer tube 29 is formed outside bottom 22 in the axial direction at the posterior end. Blunt needle retainer tube 29 has a lumen the same size as hole 22a. Movable blunt needle 10 is retained so that it can move in an axial direction by means of hole 22a positioned at bottom 22 and blunt needle retainer tube 29. In other words, in embodiment 1, hole 22a of bottom 22 and blunt needle retainer tube 29 are equivalent to the blunt needle retainer of the present disclosure. The reason why blunt needle retainer 29 is provided is to make the length of the axis direction of the movable blunt needle section longer, which improves stability for retaining movable blunt needle 10. By lengthening blunt needle retainer tube 29, radial vibration of movable blunt needle 10 can be inhibited. In addition, the diameter of blunt needle retainer tube 29 is constructed in embodiment 1 so that the outer diameter becomes smaller in tiers towards the posterior end. This is to increase the contact area of link section 30, and to improve the reliability of the adhesion and welding of outer cylinder 20 and link section 30, and is illustrative and not restrictive. Alternately, movable blunt needle 10 may be retained by hole 22a of bottom 22, without having blunt needle retainer tube 29.

At the tip periphery of outer cylinder 20, a lock section 26 is demarcated by a groove portion 23, which is adapted to lock and link to female connector 200. In the embodiment, the groove portion 23 and locking section 26 are established at two opposite positions to the circumferential direction of outer cylinder 21. Groove portion 23 includes a notch 23a facing the posterior end from the axial front end of outer cylinder 21, and a notch 23b, facing the circumferential direction in succession of notch 23a, which can be mated with projection 72 (discussed below) of female connector 200.

Locking section 26 of outer cylinder 20 is located at the rear of groove 23 and is formed of a locking surface 24, and a hook surface 25 extending from the locking surface 24. The locking surface which is positioned between hook surface 25 and projection 72, to be discussed later, should be formed linearly. In addition, locking surface 24 and hook surface 25 should be formed by the configuration of sharp angles. Also, locking surface 24 should be formed perpendicular to the axial direction so that it can correspond to axial tension. In addition, diagonally opposite the intersection surface of locking surface 24 and hook surface 25, a recessed arc surface 27 is formed in an arced state at groove portion 23.

Where junction 30 connects with the end of outer cylinder body 20 and the end of connection 40 it cooperates with connection 40 to maintain valve 50. Junction 30, includes in order a front section 31, a mid section 32 and a rear section 33 configured in a stepwise configuration in which the diameter of front section 31 is greater than the diameter of mid section 32 which is greater than the diameter of rear section 30. However, each section has roughly a cylindrical shape. The diameter of front section 31 is almost the same diameter as the front of connection 40, tip section 43 of connection 40 and outer cylinder 21. The diameter of mid section 32 is almost the same as the inner diameter of front section 43 of connection 40. The outer wall of mid section 32 is glued by an adhesive on the inner wall of front section 43. The outer diameter of rear section 33 is configured smaller than the outer diameter of mid section 32. Therefore, between the outer wall of rear section 33 and the inner wall of front section 43 of connection 40, a space (gap) is formed. This space is the valve section which is adapted to receive valve 50.

Connection 40 is connectable to tubular bodies other than tube 5 such as catheters and syringes, and is shaped to be almost cylindrical. In embodiment 1, by inserting tube 5 at tube junction 41 located at the rear section of connection 40, tube 5 is connected to male connector 100. However, the connection aspect of tube 5 is illustrative and not restrictive. For example, a female lure connector can be formed at the interior of connection 40, or a male screw can be made at the outer surface of connection 40. Also, at the interior of section 40, fluids can be distributed through distribution channel 42. Front section 43 of connection 40 is configured as almost the same outer cylindrical diameter as outer cylinder 21. A mid section 44 is formed to gradually expand the outer diameter where tube junction 41 is connected with front section 43 whose outer diameter is larger than that of the tube linking section.

Valve 50 seals the flow channel inlet of movable blunt needle 10. In other words, closure of the axial direction posterior end by junction 30 and connection 40 is maintained by valve 50. More specifically, valve 50 is disposed at the annular gap formed between the outer wall of rear section 33 of connection 30 and, the inner wall of front section 43 of connection 40. Inserting rib 52 which was constructed in order to stand on the periphery of valve 50 secures valve 50 in place.

Valve 50 is made from elastic material (e.g. plate rubber) and the center opens and closes by stretching to form a stretch hole section 51. Valve 50 opens stretch hole 51 when a predetermined amount of force is applied to it and shrinks and closes stretch hole 51 by releasing the force. Stretch hole 51 is biased closed in this way. When stretch hole 51 closes, the flow opening of movable blunt needle 10 is blocked and drug solution from distribution channel 42 to movable blunt needle 10 stops flowing.

The material of male connector 100 may include but is not limited to, for example, resins such as polypropylene and polycarbonate. (excluding valve 50). In addition, junction 30 and connection 40 can be made from resins (e.g. polycarbonate) that can obtain high dimensional precision molding. Outer cylinder body 20 which maintains the mobility of movable blunt needle 30 could be built with resin sliding (e.g. Polyacetal). In this way resin properties utilized by male connector 100 can be obtained. In addition, by using high transparency polycarbonate in outer cylinder 20, junction 30, and connection 40, visibility of medicinal liquids through the interior can be improved. Also, movable blunt needle 10 may include a superior drug-resistant polypropylene.

In addition, outer cylinder 20 and junction 30 may be monolithically formed so long as the mobility between movable blunt needle 10 and junction 40 in the axial direction is maintained and valve 50 is operable.

In this way when the movable blunt needle 10 of the male connector 100 is located at the axial tip, as shown in FIG. 3A, flange 13 is in contact with blunt needle retainer 29 of outer cylinder 20 and stops distal movement of the movable blunt needle towards the axial tip.

FIGS. 4A-D show female connector 200 of the present disclosure; FIG. 4A shows a front surface, FIG. 4B shows side surface, FIG. 4C shows a rear surface, and FIG. 4D shows a cross-section of FIG. 4B. Female connector 200 includes housing 71 which has almost the same cylindrical shape and septum 81. In FIG. 4B, the right side of the figures is the front end and the left side of the figures, the posterior end.

Housing 71 is made of a compound resin and has a cylindrical shape. The axial tip and rear of housing 71 have an established opening. At the interior front of housing 71, connection tube 73 is built almost coaxially relative to housing 71 and forms an overlapping tube section with housing 71. Connection tube 73 connects with female connector 200 and tube 7 by being inserted into the lumen of tube 7. At the inner surface tip of housing 71, there is female screw 75. Female screw 75 is a screwed connection for receiving tube 7. The internal end of housing 71 has a septum accommodation section 74 which can accommodate septum 81.

At the outer surface of housing 71, at least 2 projections 72 are formed and extend in opposed directions. Projections 72 can be mated with groove 23 of male connector 100 and secured to locking section 26. The locking surface of the projection 72 should be formed linearly with hooked surface 25 of male connector 100 so that the two can be engaged linearly. Furthermore, projection 72, locking surface 24 of male connector 100 and hook surface 25, should mate by a gradual connection. The number of projections 72 on housing 71 at an opposing radial position should be with more than one pair, but should not limited to any specific number. For example a single projection 72, a pair of projections 72 or more projections 72 could be provided. In this way a biased state of engagement with male connector 100 can be prevented.

Septum 81 includes an elastic body such as that composed of rubber or thermoplastic elastomer and is installed at septum accommodation section 74 in the vicinity of the rear opening of housing 71. At the center of septum 81, there is slit 82 that is adapted for insertion of blunt needle section 11 of movable blunt needle 10 of male connector 100. Septum 81 is adapted for the reception of movable blunt needle section 11 and for sealing the rear opening of housing 71 after withdrawal of movable blunt needle section 11 due to elastic force. Also, the thickness of the axial direction of septum 81 maintains a seal until locking section 26 of the male connector and projection 72 of the female connector are in an engaged state. Slit 82 opens and fluids are distributed by movable blunt needle 10 and connection tube 73.

Holding member 76, as shown in FIG. 4A, if seen from the front shows a donut outside the rear opening of housing 71 which is mounted to cover the edges of the rear opening of housing 71. Holding member 76, inhibits the separation of the septum 81 from the rear opening of housing 71. At the center of holding member 76 there is a round shaped hole through which movable blunt needle 10 can be inserted into septum 81.

Figure 5:
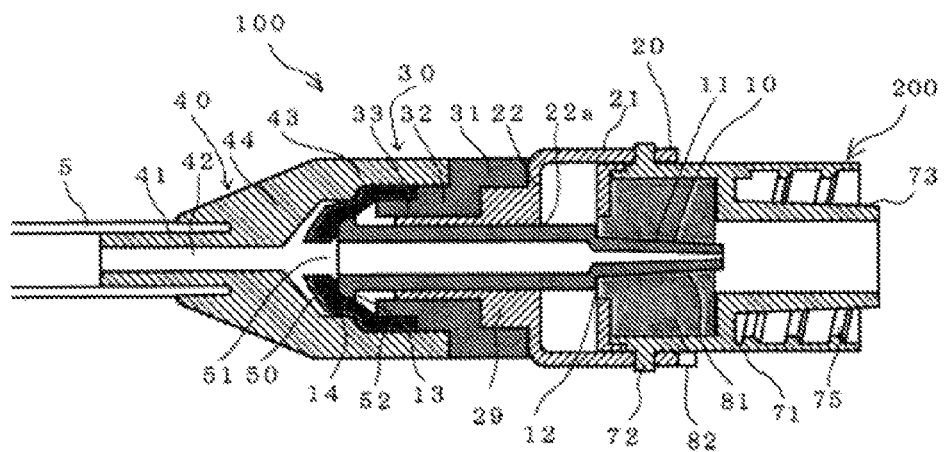
FIG. 5 is a cross-section of the male and female connectors assembled according to embodiment 1.

In a transfusion line connection device according to the present disclosure, the connection of male connector 100 and female connector 200 will be explained. FIG. 5 is a cross-sectional schematic of the connection status of male connector 100 and female connector 200. In FIG. 5 the right side of the figure is the axial front, the left side of the figure is the axial rear.

When male connector 100 is connected with female connector 200, the movable blunt needle section 11 of movable blunt needle 10 of male connector 100 is inserted into slit 82 of female connector 200 compressing male connector 100. Then blunt needle section 11 pierces slit 82 of septum 81 to open septum 81. Then, movable blunt needle 10 moves towards the axial rear due to friction with the outside wall of needle section 11 and slit 82. Furthermore, shoulder 12 of movable blunt needle 10 contacts with the surface of septum 81 of female connector 200 and is forced towards the axial rear. Housing 71 is also inserted on the inside of the outer cylinder body 20 of male connector 100.

While projection 72 of female connector 200 is mated in groove 23 of male connector 100, female connector 200 and male connector 100 approach towards each other and rotate in a circumferential direction. That way, projection 72 of female connector 200 progresses into groove 23, and locks locking section 26 to projection 72. This regulates the location of projection 72. Linear surface 72a of projection 72 is linearly connected with locking surface 24, linear surface 72b is linearly connected with hooked surface 25, and truncated outer edge 72c connects with arc 27. Locking surface 24 regulates movement of projection 72 in the axial direction and hooked surface 25 regulates movement of projection 72 in the circumferential direction. Thus male connector 100 and female connector 200 are connected in a stable state. Because of this, even if male connector 100 and female connector 200 shift, disengagement is prevented and the connection of male connector 100 and female connector 200 remains stable. In addition, locking surface 24 and hooked surface 25 of locking section 26 are formed at an acute angle such that projection 72 engages locking surface 24 and hooked surface 25 in a fitted state. Therefore, the likelihood that projection 72 will become disengaged from locking section 26 is reduced. This can further stabilize the connection of male connector 100 and female connector 200.

In addition, the septum 81 of female connector 200 receives movable blunt needle 10 of male connector 100 and by virtue of the elasticity of septum 81, projection 72 is engaged against locking surface 24 in the axial front direction. Therefore, the engagement of locking surface 26 and the projection 72 is made stronger.

In this way if locking section 26 of male connector 100 receives projection 72 of female connector 200, as FIG. 5 shows, movable blunt needle 10 moves towards the axial rear of male connector 100 and valve 50 and compression surface 14 presses against valve 50 to open stretch hole 51 of valve 50. This causes the inlet passage of movable blunt needle 10 to be in the open state. Furthermore, movable blunt needle 10 penetrates septum 81. Because stretch hole 51 and septum 81 are both open liquid becomes distributable between male connector 100 and female connector 200. In addition, since movable blunt needle 10 presses against valve 50 and at the opened stretch hole 51 and shoulder 12 of movable blunt needle 10 presses against the surface of septum 81 of female connector 200, movement towards the axial front of movable blunt needle 10 is regulated and the connection state of female connector 200 and male connector 100 is stabilized. In addition, the valve compression surface 14 of movable blunt needle 10 is smoothly chamfered such that when valve compression surface 14 is pressed against valve 50, damage to valve 50 is inhibited.

When the connection between male connector 100 and female connector 200 is released, male connector 100 and female connector 200 compress towards each other to remove hooked surface 25 from projection 72 and are rotated in the opposite direction as compared to when connecting male connector 100 and female connector 200 are connected together. As previously stated, locking section 26 and projection 72 of male connector 100 and female connector 200 have a stable connection axially and circumferentially. However it is possible for movable blunt needle 10 to move axially when male connector 100 and female connector 200 are compressed such that the male connector 100 can further receive the female connector 200. Thus, when male connector 100 and female connector 200 are being disconnected, and male connector 100 and female connector 200 are pressed towards each other the burden on the user can be reduced resulting in easy disconnection. In addition, outer section 72c of projection 72 and arc surface 27 press together since they are in an arced state while locked section 26 and projection 72 are sliding such that the lock can be released and is easy to remove.

In addition, since the connection state of male connector 100 and female connector 200 is fixed by locking section 26 and projection 72 in the connection state the distance between male connector 100 and female connector 200 is kept constant. Thus, by the engagement of locking section 26 and projection 72 overinsertion or underinsertion towards female connector 200 can be inhibited. The liquid between male connector 100 and female connector 200 can have a stable distribution.

As discussed above with regard to the male connector 100 of embodiment 1, there is an internal flow path through the movable blunt needle 10 in which liquid is distributable. The internal flow path is formed by hole 22a of bottom section 22 and blunt needle retainer tube 29 and axial movement maintenance is made possible by the formed needle holding section. The flow mouth of movable blunt needle 10 is blocked until movable blunt needle 10 moves axially to press against and open valve 50. Thus, when inserting movable blunt needle 10 into female connector 200 movable blunt needle 10 moves axially and opens valve 50. In the open state of the flow mouth of movable blunt needle 10 shoulder 12 presses against female connector 200. Thus, the distribution of liquids such as drugs between male connector 100 and female connector 200 is made possible. In addition, when shoulder 12 presses against female connector 200 the axial movement of movable blunt needle 10 is regulated and the connection state of male connector 100 and female connector 200 is stabilized. Then, when male connector 100 is removed from female connector 200, movable blunt needle 10 is no longer pressed against valve 50 and valve 50 closes stopping the flow of liquid through movable blunt needle 10. Therefore, even when male connector 100 is removed from female connector 200, no fluid leaks. Therefore, connecting male connector 100 and female connector 200 or withdrawal when working or during priming, liquid discharge to the caster can be inhibited. Also, even when male connector 100 disconnects from female connector 200 involuntarily since there are no leaks, it takes no time to clean sheets or the floor due to leaks since no liquids will be spilled wastefully.

In addition, when movable blunt needle 10 moves axially, in other words, when a connection of male connector 100 and female connector 200 is formed, junction 30 and connection section 40 restrain valve 50 such that the connection is stable. Thus, junction 30 and connection section 40 inhibit the amount of deformation of that valve 50 can undergo thereby inhibiting a reduction in the amount of resistance provided by valve 50 to movable blunt needle 10.

In addition outer cylinder body 20 surrounds movable blunt needle 10 and includes an axially lockable locking surface 24 for the reception of projection 72 of female connector 200 and a locking section 26 which has a circumferentially lockable hook surface 25. When projection 72 of female connector 200 is locked at locking section 26 of male connector 100, movable blunt needle 10 moves axially opening valve 50. Since when male connector 100 and female connector 200 are connected, projection 72 and locking section 26 are in a locked state, involuntary withdrawal by the user of male connector 100 and female connector 200 is inhibited. Also, since the distance between male connector 100 and female connector 200 can be made constant when in a connected state, the distribution of liquid between male connector 100 and female connector 200 can be stabilized.

The embodiment 1 shows female connector 200 as the destination of connection for male connector 100, however, it is illustrative and not restrictive. For example, a three-way stopcock equipped with a septum in which the movable blunt needle can be inserted, can also be used.

Embodiment 2

In embodiment 2, there is disclosed an example of a movement regulation component which regulates excessive axial movement of movable blunt needle 10A of the male connector 100. Embodiment 2 mainly describes the differences with embodiment 1 and identical or corresponding structure as that of embodiment 1 is given similar symbols.

Figure 6A:
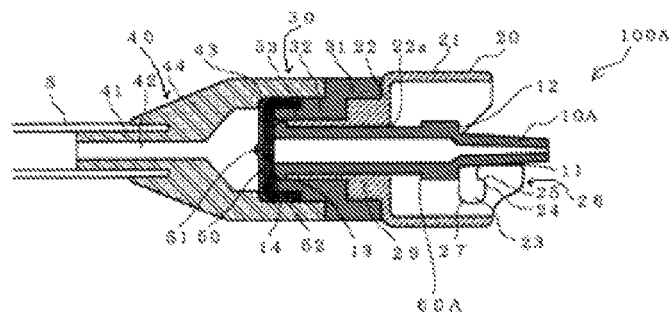
FIG. 6A is a cross-section of the male connector according to embodiment 2.
Figure 6B:
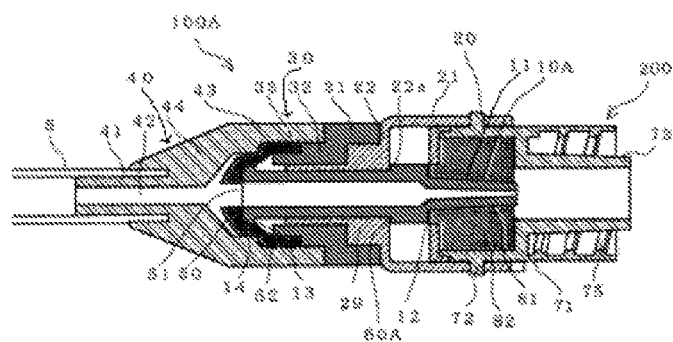
FIG. 6B is a cross-section of the male and female connectors according to embodiment 2.

FIGS. 6A and 6B are figures that show the connection device of the infusion line of embodiment 2, FIG. 6A shows a cross-sectional schematic view of male connector 100, FIG. 6B shows a cross-sectional schematic of the connection state of male connector 100A and female connector 200. As FIGS. 6A and 6B show, the outer diameter of movable blunt needle 10A has a smaller diameter at a predetermined position in the axial direction at the posterior end relative to shoulder 12 and has a larger diameter as compared with the inner diameter of the blunt needle retainer tube 29 at shoulder 12. The part where the outer diameter is larger than blunt needle retainer tube 29 is movement regulation component 60A.

When movable blunt needle 10A is axially moved such that valve 50 is in a predetermined open state the front of the blunt needle retainer and the opening surface (bottom section 22) of hole 22a is contacted by movement regulation component 60A and the axial movement of movable blunt needle 10A is limited. As shown in FIG. 6B, when connecting male connector 100A and female connector 200, movement regulation component 60A extends from shoulder 12 across the space between septum 81 of female connector 200 and bottom section 22 of male connector 100A and engages septum 81 and bottom section 22. Basically, the distance between the surface section and the locked surface 24 of bottom section 22, the distance between movement regulation component 60A to shoulder 12 and the distance from septum 81 to the tip of projection 72 (as shown in FIG. 6B on the right side of the figure) are configured to be less than the sum of the distances. Thus, locking projection 72 in locking surface 24 locks female connector 200 and male connector 100A in connection and shoulder 12 presses against the surface of septum 81 to ensure contact and pushes movable blunt needle 10A axially to ensure the opening of valve 50. Other uses and configurations are the same as embodiment 1.

As discussed above, Embodiment 2 is equipped with a movement regulation component 60A at the outer circumferential section of movable blunt needle 10A, where contacting the needle holding section by moving movable blunt needle 10A axially is regulated when movable blunt needle 10A axially moves resulting in valve 50 being in an open state. Thus, in addition to the effects shown in embodiment 1, excessive axial movement of movable blunt needle 10A and excessive opening of valve 50 are inhibited. Since there is no excessive opening of valve 50, damage to stretchable hole 51 of valve 50 or encouragement of settling of valve 50 can be avoided.

Embodiment 3

Figure 7:
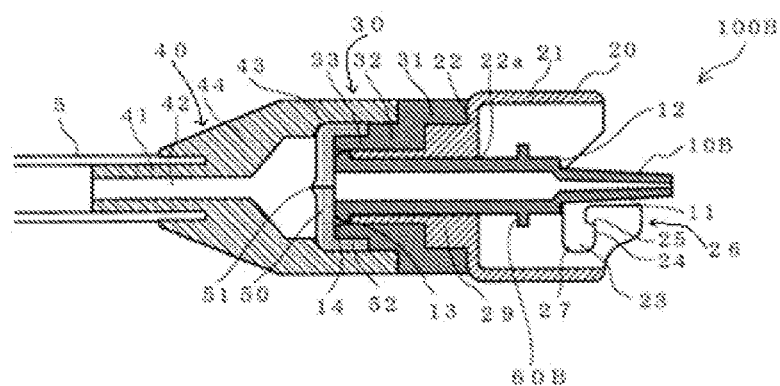
FIG. 7 is a cross-section of the male connector according to embodiment 3.

Embodiment 3 discloses configuration examples other than the movement regulation component established in the movable blunt needle of the male connector. FIG. 7 is a schematic cross-section of male connector 100B according to embodiment 3. Embodiment 3 mainly explains the differences with embodiment 2 and identical or corresponding structure as that of embodiments 1 and 2 is given similar symbols.

Instead of shoulder 12, movable blunt needle 10B includes a movement regulation component 60B disposed in a predetermined position of axial movement. In embodiment 3, movement regulation component 60B of movable blunt needle 10B is a projection projecting outward circumferentially from movable blunt needle 10B. At least two of the projections (one pair) of movement regulation component 60B are disposed at an opposing position of the circumferential position of movable blunt needle 10B. When valve 50 is in an open state due to the axial movement of movable blunt needle 10B, the movement regulating components 60B are contacted with the opening surface of the hole 22a (bottom section 22) and the axial movement of movable blunt needle 10B is limited.

As discussed above, the effect of movement regulation component 60B of the male connector 100B of embodiment 3 may also be performed by embodiment 2.

Embodiment 4

Figure 8:
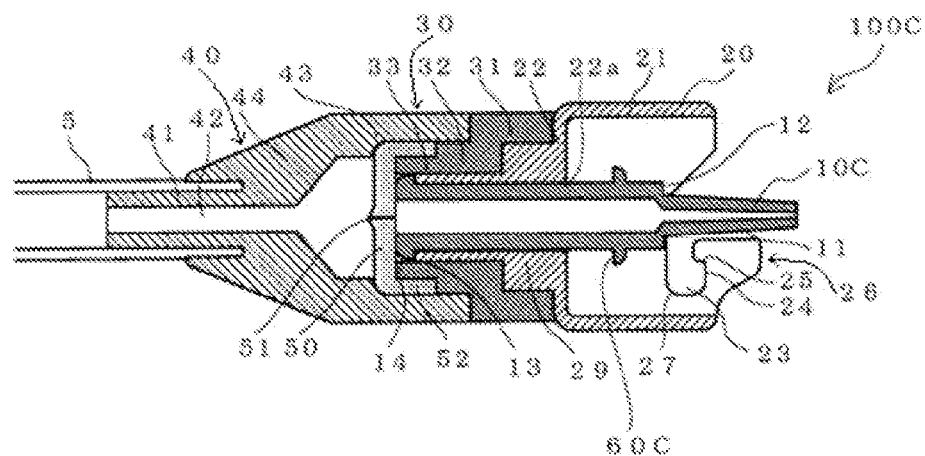
FIG. 8 is a cross-section of the male connector according to embodiment 4.

Embodiment 4 discloses configuration examples other than the movement regulation component in the movable blunt needle of the male connector. FIG. 8 is a schematic cross-section of the male connector 100C according to embodiment 4. Embodiment 4 mainly explains the differences with embodiment 2 and identical or corresponding structure as that of embodiments 1 and 2 is given similar symbols.

Instead of shoulder 12, movable blunt needle 10C includes movement regulation component 60C in a predetermined position of axial movement. In embodiment 4, movement regulation component 60C includes a flange projecting in a flanged state towards the circumferential side of movable blunt needle 10C. The flange of movement regulation component 60C forms a circle around the outer circumference of movable blunt needle 10C. However, the length of the circle is not necessarily limited. When valve 50 is opened by the axial movement of movable blunt needle 10C, regulation component 60C contacts the opening surface of hole 22a (bottom section 22) and the axial movement of movable blunt needle 10C is limited.

As discussed above, the effect of movement regulation component 60C of the male connector 100C of embodiment 4 may also be performed by embodiment 2.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A male connector for a transfusion line comprising:
   an outer body defining a hole therethrough for the reception of fluids and including a locking member adapted to secure a corresponding connector to the outer body;
   a link section attached to the outer body and extending proximally from the outer body;
   a junction defining a fluid passageway therethrough for the reception of fluids, the junction attached to the link section and defining a space therebetween;
   an elongate member at least partially disposed within the hole and axially movable relative to the hole, the elongate member defining a lumen therethrough for the reception of fluids; and
   a sealing member disposed between the elongate member and the passageway of the junction, at least a portion of the sealing member being secured within the space between the junction and the link section, the sealing member being biased towards a closed state and transitionable between the closed state and an open state upon movement of the elongate member relative to the hole of the outer body, wherein a tip portion of the elongate member extends axially beyond the outer body when the sealing member is in the closed state.

2. A male connector according to claim 1, wherein a proximal end of the elongate member includes a chamfered surface, the chamfered surface adapted to minimize damage to the sealing member upon contact with the sealing member.

3. A male connector according to claim 1, wherein the sealing member is transitioned to the open state upon movement of the elongate member in a proximal direction relative to the hole of the outer body.

4. A male connector according to claim 1, wherein the tip portion of the elongate member is adapted for insertion into the corresponding connector.

5. A male connector according to claim 4, wherein the elongate member includes a shoulder extending radially outward from the tip portion, the shoulder being adapted to move the elongate member relative to the hole of the outer body upon contact with an outer surface of a female connector to transition the sealing member from the closed state to the open state.

6. A male connector according to claim 1, wherein the outer body, link section and junction are transparent.

7. A male connector according to claim 1, wherein elongate member includes a flange extending from a proximal portion of the elongate member, the flange being adapted to abut a distal end of the outer body when the sealing member is in the closed state.

8. A male connector according to claim 1, wherein the locking member is adapted to receive a projection of the corresponding connector.

9. A male connector according to claim 8, wherein the locking member receives the projection upon rotation of the corresponding connector relative to the outer body.

10. A male connector according to claim 1, wherein a portion of the elongate member includes a movement regulating component which extends radially outward from the elongate member and is adapted to limit the axial movement of the elongate member relative to the hole of the outer body.

11. A male connector according to claim 10, wherein the movement regulating component presses against an outer surface of the hole when the sealing member is in the open state.

12. A transfusion line set comprising:
    a female connector comprising:
      a housing including an opening extending therethrough and at least one projection extending from an outer surface of the housing; and
      a seal disposed within the housing at a proximal end of the housing;
    a male connector comprising:
      an outer body defining a hole therethrough and including a locking member adapted to receive the projection of the female connector in a secure manner;
      a link section attached to the outer body and extending proximally from the outer body;
      a junction defining a fluid passageway therethrough, the junction attached to the link section and defining a space therebetween;
      an elongate member at least partially disposed within the hole and axially movable relative to the hole, the elongate member defining a lumen therethrough and a tip portion adapted for insertion through the seal of the female connector; and
      a sealing member disposed between the elongate member and the passageway of the junction, at least of portion of the sealing member being secured within the space between the junction and the link section, the sealing member being biased in a closed state and transitionable between the closed state and an open state upon movement of the elongate member relative to the hole of the outer body.

13. A transfusion line set according to claim 12, wherein the elongate member includes a shoulder extending radially outward from the tip portion, the shoulder adapted to move the elongate member axially upon contact with an outer surface of the seal of the female connector.

14. A transfusion line set according to claim 12, wherein a portion of the elongate member includes a movement regulating component extending radially outward from the elongate member and adapted to limit the axial movement of the elongate member relative to the hole of the outer body.

15. A transfusion line set according to claim 14, wherein the movement regulating component presses against an outer surface of the hole when the sealing member is in the open state.

16. A transfusion line set according to claim 15, wherein the movement regulating component presses against an outer surface of the seal of the female connector when the sealing member is in the open state.

17. A transfusion line set according to claim 12, wherein the locking member includes a groove portion adapted to receive the at least one projection of the female connector to secure the female connector to the male connector.

18. A transfusion line set according to claim 17, wherein the groove portion includes a hooked surface adapted to engage a locking surface of the at least one projection of the female connector in a linear manner.

19. A transfusion line set according to claim 12, wherein when the tip portion of the elongate member is inserted through the seal of the female connector, the elongate member moves relative to the outer body to press against and transition the sealing member to the open state thereby allowing fluid to flow between the male connector and the female connector.

20. A transfusion line set according to claim 12, wherein the sealing member is biased towards the closed state.

* * * * *